(12) United States Patent
Peskar et al.

(10) Patent No.: US 9,555,598 B2
(45) Date of Patent: *Jan. 31, 2017

(54) FOAM CUSHION FOR HEADPHONES

(71) Applicant: HEARING COMPONENTS, INC., Oakdale, MN (US)

(72) Inventors: Justin C. Peskar, Eagan, MN (US); William L. Parish, Maplewood, MN (US)

(73) Assignee: Hearing Components, Inc., Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,315

(22) Filed: Feb. 4, 2016

(65) Prior Publication Data
US 2016/0152000 A1    Jun. 2, 2016

Related U.S. Application Data

(63) Continuation of application No. 14/628,468, filed on Feb. 23, 2015, now Pat. No. 9,254,227, which is a
(Continued)

(51) Int. Cl.
*H04R 1/08* (2006.01)
*B32B 5/20* (2006.01)
(Continued)

(52) U.S. Cl.
CPC ............... *B32B 5/20* (2013.01); *A61F 11/14* (2013.01); *B29C 44/146* (2013.01); *B32B 25/045* (2013.01); *B32B 25/08* (2013.01); *B32B 25/14* (2013.01); *B32B 27/065* (2013.01); *B32B 27/08* (2013.01); *B32B 27/26* (2013.01); *B32B 27/40* (2013.01); *H04R 1/1008* (2013.01); *B29K 2105/24* (2013.01); *B29K 2995/0002* (2013.01);
(Continued)

(58) Field of Classification Search
CPC ..................................................... H04R 1/1008
USPC .......................................................... 181/229
See application file for complete search history.

(56) References Cited

U.S. PATENT DOCUMENTS 3,030,458 A    4/1962  Gongoll
3,051,961 A    9/1962  Clark
(Continued)

FOREIGN PATENT DOCUMENTS

EP    0780440 A2    6/1997
WO    9748296 A1    12/1997
WO    9847684 A1    10/1998

*Primary Examiner* — Forrest M Phillips
(74) *Attorney, Agent, or Firm* — Seager, Tufte & Wickhem LLP

(57) ABSTRACT

A composite foam cushion for a sound control device. The cushion includes a core formed of a polymeric foam material and a polymeric coating overlying at least a portion of the core of polymeric foam material. The polymeric coating includes an outer coating layer and an inner polymeric coating layer bonded to the core of polymeric foam material. The inner coating layer may provide the cushion with strength, while providing a high degree of flexibility and suppleness to closely conform around contours and obstructions. The outer coating layer may provide the cushion with enhanced abrasion resistance and/or chemical resistance while having an aesthetically pleasing feel and appearance.

20 Claims, 15 Drawing Sheets

Related U.S. Application Data continuation of application No. 14/290,476, filed on May 29, 2014, now Pat. No. 8,960,366, which is a continuation of application No. 13/646,405, filed on Oct. 5, 2012, now Pat. No. 8,746,397.

(60) Provisional application No. 61/545,009, filed on Oct. 7, 2011.

(51) Int. Cl.

| | | |
|---|---|---|
| *A61F 11/14* | (2006.01) | |
| *B29C 44/14* | (2006.01) | |
| *H04R 1/10* | (2006.01) | |
| *B32B 25/04* | (2006.01) | |
| *B32B 25/08* | (2006.01) | |
| *B32B 25/14* | (2006.01) | |
| *B32B 27/06* | (2006.01) | |
| *B32B 27/08* | (2006.01) | |
| *B32B 27/26* | (2006.01) | |
| *B32B 27/40* | (2006.01) | |
| *B29K 105/24* | (2006.01) | |

(52) U.S. Cl.
CPC ........ *B32B 2250/03* (2013.01); *B32B 2250/24* (2013.01); *B32B 2266/0278* (2013.01); *B32B 2307/554* (2013.01); *B32B 2307/56* (2013.01); *B32B 2457/00* (2013.01); *Y10T 428/24355* (2015.01); *Y10T 428/24446* (2015.01); *Y10T 428/249991* (2015.04)

(56) References Cited

U.S. PATENT DOCUMENTS

| | | |
|---|---|---|
| 3,571,813 A | 3/1971 | Allen |
| 4,071,717 A | 1/1978 | Fidi |
| 4,170,275 A | 10/1979 | Larsen |
| 4,572,324 A | 2/1986 | Fidi et al. |
| 4,674,134 A | 6/1987 | Lundin |
| 4,774,938 A | 10/1988 | Leight |
| 4,809,811 A | 3/1989 | Gorike |
| 4,856,118 A | 8/1989 | Sapiejewski |
| 4,958,697 A | 9/1990 | Moody |
| 4,989,271 A | 2/1991 | Sapiejewski et al. |
| 5,020,163 A | 6/1991 | Aileo et al. |
| 5,089,189 A | 2/1992 | Staneluis et al. |
| 5,138,722 A | 8/1992 | Urella et al. |
| 5,400,296 A | 3/1995 | Cushman et al. |
| 5,420,381 A | 5/1995 | Gardner et al. |
| 5,704,069 A | 1/1998 | Andersson |
| 5,821,468 A | 10/1998 | Urella et al. |
| 5,920,911 A | 7/1999 | Cushman |
| 5,970,160 A | 10/1999 | Nilsson et al. |
| 5,979,451 A | 11/1999 | Leight |
| 6,163,615 A | 12/2000 | Callahan |
| 6,412,593 B1 | 7/2002 | Jones |
| 6,683,965 B1 | 1/2004 | Sapiejewski |
| 6,684,976 B1 | 2/2004 | Sheppard, Jr. |
| 6,856,690 B1 | 2/2005 | Skulley |
| 7,245,736 B2 | 7/2007 | Tsunoda et al. |
| 7,444,687 B2 | 11/2008 | Sato et al. |
| 7,489,795 B2 | 2/2009 | Ito |
| 7,580,539 B2 | 8/2009 | Tachikawa |
| 7,853,034 B1 | 12/2010 | Gresko |
| 7,854,294 B2 | 12/2010 | Du et al. |
| 8,746,397 B2 | 6/2014 | Peskar et al. |
| 8,960,366 B2 | 2/2015 | Peskar et al. |
| 9,254,227 B2 * | 2/2016 | Peskar .................. A61F 11/14 |
| 2003/0034198 A1 | 2/2003 | Cushman |
| 2005/0273910 A1 | 12/2005 | Cozens et al. |
| 2005/0283882 A1 | 12/2005 | Berger et al. |
| 2006/0269090 A1 | 11/2006 | Sapiejewski |
| 2007/0121984 A1 * | 5/2007 | Chen .................. H04R 1/1033 381/367 |
| 2007/0223719 A1 * | 9/2007 | Huang ................ H04R 1/1041 381/74 |
| 2010/0128884 A1 | 5/2010 | Sapiejewski et al. |
| 2010/0158301 A1 | 6/2010 | Kuhtz et al. |
| 2010/0167033 A1 | 7/2010 | Poppe et al. |
| 2011/0188696 A1 | 8/2011 | Kimura |
| 2013/0087404 A1 | 4/2013 | Peskar et al. |

\* cited by examiner

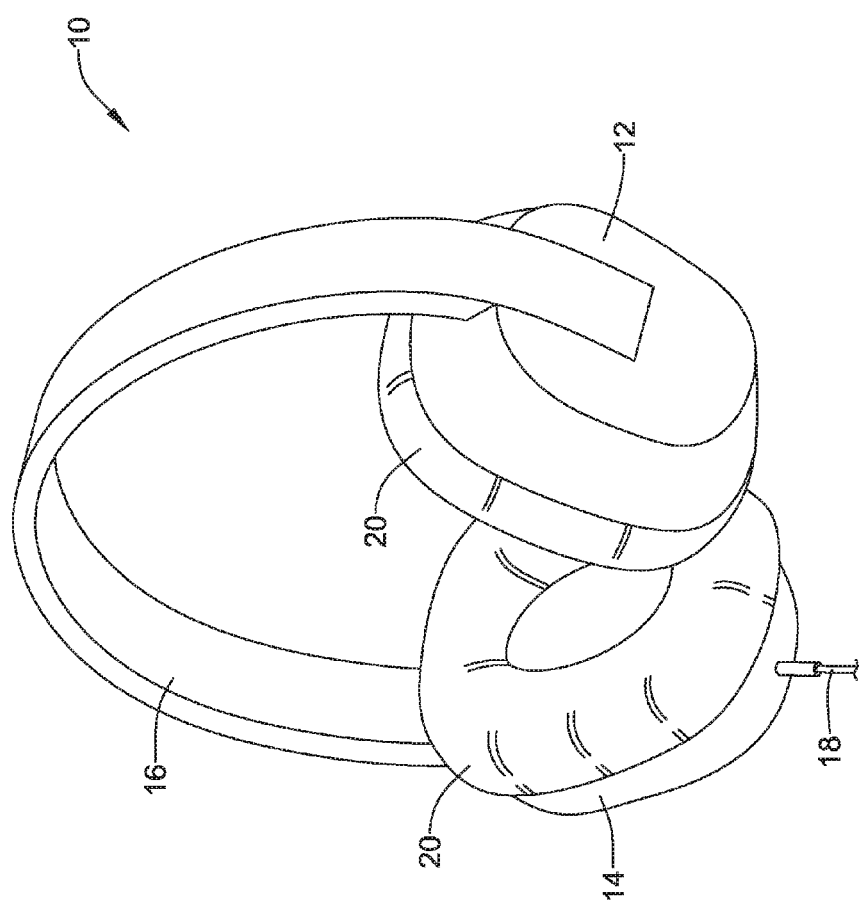

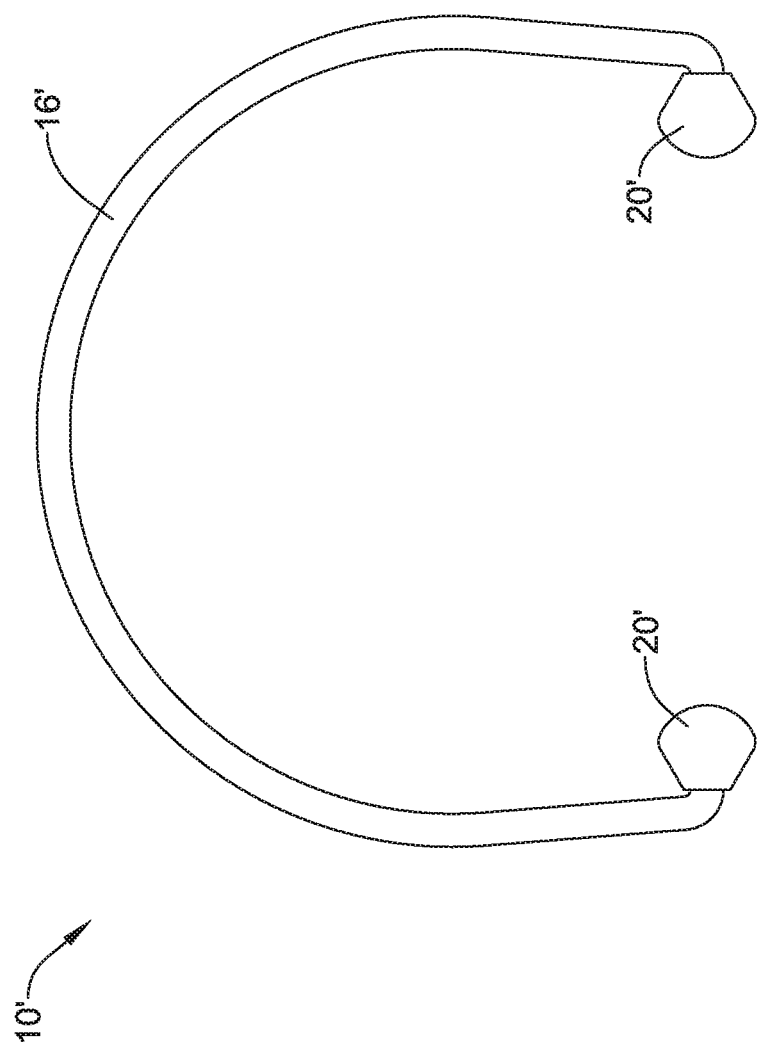

FOAM CUSHION FOR HEADPHONES

CROSS-REFERENCE TO RELATED APPLICATIONS

The present application is a continuation application of U.S. patent application Ser. No. 14/628,468, filed Feb. 23, 2015 which is a continuation of U.S. patent application Ser. No. 14/290,476, filed May 29, 2014, now U.S. Pat. No. 8,960,366 which is a continuation of U.S. patent application Ser. No. 13/646,405, filed Oct. 5, 2012, now U.S. Pat. No. 8,746,397, which claims priority to U.S. Provisional Application No. 61/545,009, filed Oct. 7, 2011, the entire disclosures of which are incorporated herein by reference.

TECHNICAL FIELD

The disclosure is directed to foam pads or cushions for use in headphones and other sound control devices. More particularly, the disclosure is directed to foam pads or cushions having enhanced suppleness while maintaining high abrasion resistance and durability.

BACKGROUND

A conventional cushioned headphone device includes a pair of cushions configured to press against a user's head and at least partially surround the outer ears of the user. In addition to isolating the user's ears from outside sounds, such cushions are intended to at least partially conform around irregularities of the head and outer ear of the user, as well an any intervening structures (e.g., eyeglass frames). However, known cushions lack the level of conformability to closely follow the contours of a user's anatomy while retaining sufficient durability to withstand continued use.

Accordingly, it is desirable to provide alternative configurations of foam cushions for headphones and earmuffs that are configured to closely conform to the user's anatomy which have an aesthetically pleasing feel and appearance, yet sufficient durability to withstand continued use.

SUMMARY

The disclosure is directed to several alternative designs, materials and methods of manufacturing foam pads or cushions for headphones, earmuffs, and other sound controlling devices.

Accordingly, one illustrative embodiment is a composite foam cushion for a sound control device. The composite foam cushion includes a core formed of a polymeric foam material and a polymeric coating overlying at least a portion of the core of polymeric foam material.

The polymeric coating may include an inner polymeric coating layer positioned outward of the core of polymeric foam material and an outer polymeric coating layer positioned outward of the inner polymeric coating layer. The inner polymeric coating layer may be bonded to the polymeric foam material of the core, and the outer polymeric coating layer may be bonded to the inner polymeric coating layer.

The composite foam cushion may have a Conformability Gap Value of 0.650 inches or less, 0.635 inches or less, 0.625 inches or less, 0.615 or less, or 0.600 inches or less.

The composite foam cushion may have an average Indentation Force Ratio of 0.090 or less, 0.085 or less, 0.080 or less, or 0.075 or less over a Protrusion Value range of 2.0 to 7.0 millimeters.

The core of polymeric foam material may have a first glass transition temperature at about −45° C. and a second glass transition temperature at about −25° to −30° C. or about −20° to −30° C.

Another illustrative embodiment is a composite foam cushion for a sound control device to be placed against the head or ear of a user. The composite foam cushion includes a core formed of a polymeric foam material and a polymeric coating overlying at least a portion of the core of polymeric foam material. The polymeric coating includes an inner polymeric coating layer positioned around at least a portion of the core of polymeric foam material and an outer polymeric coating layer disposed over at least a portion of the inner polymeric coating layer. The inner polymeric coating layer is formed of a polymeric composition including a crosslinker, and the outer polymeric coating layer is formed of a polymeric composition including a crosslinker. The inner polymeric coating layer is less crosslinked than the outer coating layer.

The crosslinker of the polymeric composition of the outer polymeric coating layer may be present in a greater weight percent than the crosslinker of the polymeric composition of the inner polymeric coating layer and/or the crosslinker of the polymeric composition of the outer polymeric coating layer may be different than the crosslinker of the polymeric composition of the inner polymeric coating layer.

Another illustrative embodiment is a composite foam cushion for a sound control device. The composite foam cushion includes a polymeric foam core formed of a foaming reaction of an isocyanate with a polyether polyol in the presence of a catalyst. The composite foam cushion also includes an inner polymeric coating layer and an outer polyurethane based polymeric coating layer chemically bonded to the inner polymeric coating layer. The outer polyurethane based polymeric coating layer is formed of a mixture of a polyurethane dispersion, a coalescing media, a wetting agent, and a crosslinker. The inner polymeric coating layer is less crosslinked than the outer polymeric coating layer.

Another illustrative embodiment is a sound control device for placement on the head of a user. The sound control device includes a pair of ear pieces with a band extending between the ear pieces. Each ear piece includes a composite foam cushion as described herein. The sound control device may include transducers or drivers fitted in the ear pieces to transmit sound into the ear canal of a user.

The core of polymeric foam material of the composite foam cushion may be a molded core formed in a molding process, and the polymeric coating of the composite foam cushion may be molded over the molded core during the molding process.

The molded polymeric coating may include an inner polymeric coating layer positioned outward of the annular core of polymeric foam material and an outer polymeric coating layer positioned outward of the inner polymeric coating layer.

Yet another illustrative embodiment is a method of forming a cushion for a sound control device. The method includes applying an outer polymeric coating layer into a cavity of a mold and applying an inner polymeric coating layer into the cavity of the mold over the outer polymeric coating layer. A polymeric foam composition is disposed into the cavity of the mold after applying the inner and outer polymeric coating layers into the cavity of the mold. The polymeric foam composition is then foamed in the cavity. The polymeric foam composition, the outer polymeric coating layer, and the inner polymeric coating layer are then cured in the cavity of the mold.

Each of the outer polymeric coating layer and the inner polymeric coating layer may be allowed to dry prior to disposing the polymeric foam composition into the cavity of the mold.

The mold may be heated to an elevated temperature of 50° C. or more before applying the outer polymeric coating layer into the cavity of the mold.

The polymeric foam composition may be controllably metered into the cavity of the mold such that when the foam composition foams, the quantity of foam composition disposed into the cavity forms a foam core having a volume substantially filling the cavity without appreciably exceeding the volume of the cavity.

The polymeric foam composition may diffuse into the inner polymeric coating layer and/or into the outer polymeric coating layer during the molding process.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIG. 1A is a perspective view of an exemplary sound control device, illustrated as a set of headphones, incorporating a cushion as described herein;

FIG. 1B is a front view of an exemplary sound control device, illustrated as a pair of ear caps, incorporating a cushion as described herein;

Figure 2:
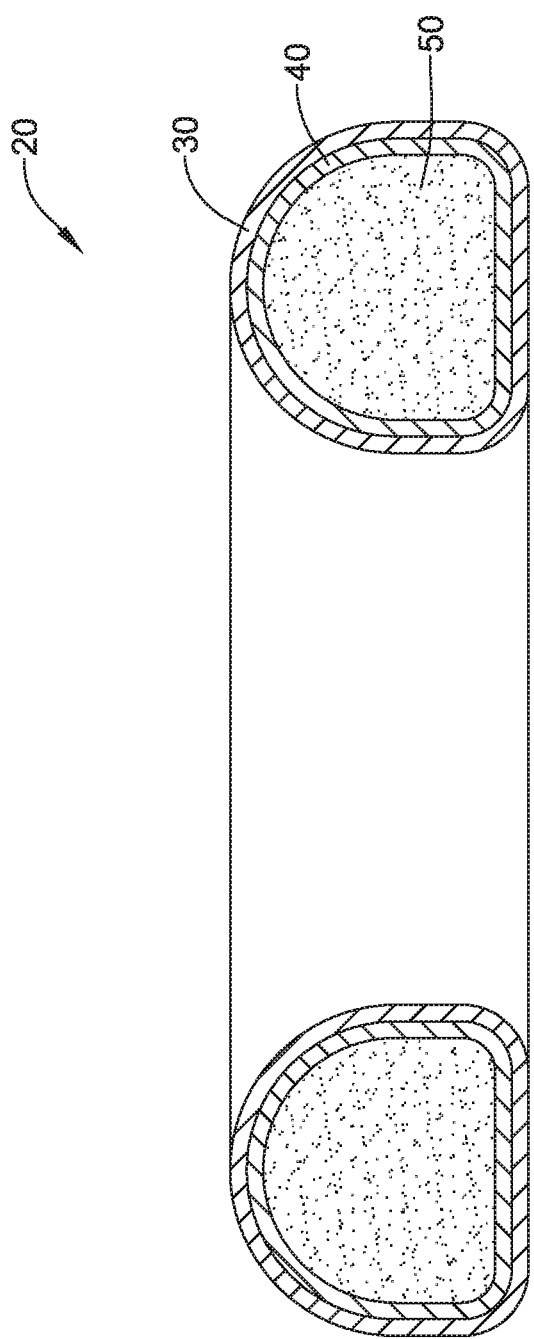
FIG. 2 is a cross-sectional view of an exemplary cushion as described herein.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1A illustrates an exemplary sound control device, in the form of headphones, headsets or earmuffs 10 utilizing foam pads or cushions 20 for secure yet comfortable placement over and/or on the ears of a user. In some instances, the sound control device 10 may be of the over-the-ear type (i.e., circumaural) configured to surround or encompass the ears of the user, or of the on-ear type (i.e., supra-aural) configured to sit on the top of the ears of the user. The sound control device 10 may include a pair of ear pieces including a pair of cups 12, 14 for placement over or on the ears of a user, and a headband or strap 16 extending between and connecting the opposing ear units 12, 14 of the headphones or earmuffs 10. The strap 16 may provide a resilient force to urge the ear pieces (e.g., the cushions 20 of the ear pieces) into contact with the head and/or ears of the user to help retain the headphones or earmuffs 10 on the user's head. The strap 16 may be curved to conform around a portion of the user's head and/or adjustable in length to accommodate different sized heads. The cushions 20 may be secured directly or indirectly to a perimeter of the cups 12, 14 by any desired means, including mechanical fasteners or devices, adhesive compositions, or other fastening mechanisms. In instances in which the sound control device 10 is a set of headphones, a cord 18 may extend from one or both of the ear pieces to provide an electrical pathway for transmitting an audio signal to transducers or drivers fitted in the ear pieces, or the transducers or drivers in the ear pieces of the headphones may wirelessly receive an audio signal.

FIG. 1B illustrates an alternative sound control device 10', in the form of ear caps, utilizing foam pads or cushions 20' for secure yet comfortable placement in the ear of a user. The sound control device 10' may include a pair of ear pieces including cushions 20' configured to rest in the concha of a user's ear to cover the ear canal, and a headband or strap 16' extending between and connecting the opposing ear pieces. The strap 16' may provide a resilient force to urge the ear pieces (e.g., the cushions 20' of the ear pieces) into contact with ears of the user to cover the user's ear canals. The strap 16' may be curved to conform around a portion of the user's head and/or adjustable in length to accommodate different sized heads. The cushions 20' may be secured directly or indirectly to the strap 16' by any desired means, including mechanical fasteners or devices, adhesive compositions, or other fastening mechanisms.

The cushions 20 may provide a sealing layer between the cups 12, 14 of the headphones, headset or earmuffs 10 and the head of the user surrounding the user's ears, sealing off unwanted sound from entering the user's ear canal and reaching the user's ear drum. For example, the cushions 20, which may be annular members, may include a layer of sound attenuating polymeric foam material 50 at an interface between a circumferential rim of the cups 14, 16 and the head of the user to prevent unwanted sounds from reaching the user's ear drums. The cushions 20 may be sufficiently supple to comfortably fit against the user's head while substantially conforming to the contours of the user's head and any intervening structure (e.g., eyeglass frames, etc.). Furthermore, the cushions 20 may be sufficiently durable and chemical resistant to insure the integrity of the cushions 20 is maintained throughout the useful life of the cushions 20.

Furthermore, in some instances, a polymeric composite foam cushion 20 as described herein, may be provided on the headband or strap 16 of a sound control device 10 to provide an interface between the sound control device and top of the user's head, for example, to improve the comfort level of the sound control device 10 on the user's head.

As mentioned above, in some instances the cushion 20 may be an annular member configured to at least partially surround the outer ear of a user. In other instances, the cushion 20 may be a disc shape, or otherwise shaped body configured to be pressed against the ear. In one such configuration, the cushion 20 may include one or more, or a plurality of openings allowing sound to pass through the cushion 20 or be provided with a porous sound transmission portion, for example. In some instances, the cushion 20 may be a thin layer attached to an intervening cushion or pad, or other structure, of a sound control device, such that the cushion 20 is arranged to provide an interface between the sound control device and the user's anatomy. A cross-section of an exemplary composite cushion 20 is shown in FIG. 2. As can be seen, the composite foam cushion 20 may include a polymeric coating or film overlying at least a portion of a polymeric foam core 50. For example, the polymeric coating or film may be disposed over and substantially surround the polymeric foam core 50. In at least some instances, the polymeric coating or film may include an outer coating or film layer 30 and an inner coating or film layer 40 disposed between the outer coating layer 40 and the polymeric foam core 50. It is noted that for illustrative purposes the thickness of the outer and inner coating layers 30, 40 is greatly exaggerated in FIG. 2.

The core 50, which may be a body of foam material, may be resiliently compressible against the head or ear of a user. For example, the polymeric foam core 50 may be formed of an open cell foam material having a desired porosity. In some instances, the polymeric foam forming the core 50 may have an open cell structure, a closed cell structure or a combination of open and closed cells. In some instances, the polymeric foam material forming the core 50 may be a slow recovery foam, having a recovery time in the range of 1 second to 60 seconds measured at 37 degrees Celsius and 50% relative humidity. In some embodiments, the polymeric foam core 50 may be formed of a polyurethane foam material having an open-cell structure. In other embodiments, the polymeric foam core 50 may be formed of another foam material, such as polyvinyl chloride (PVC), for example, a plasticized polyvinyl chloride foam. Although some suitable materials have been identified, other suitable polymers may be found useful for forming the core 50.

Figure 3:
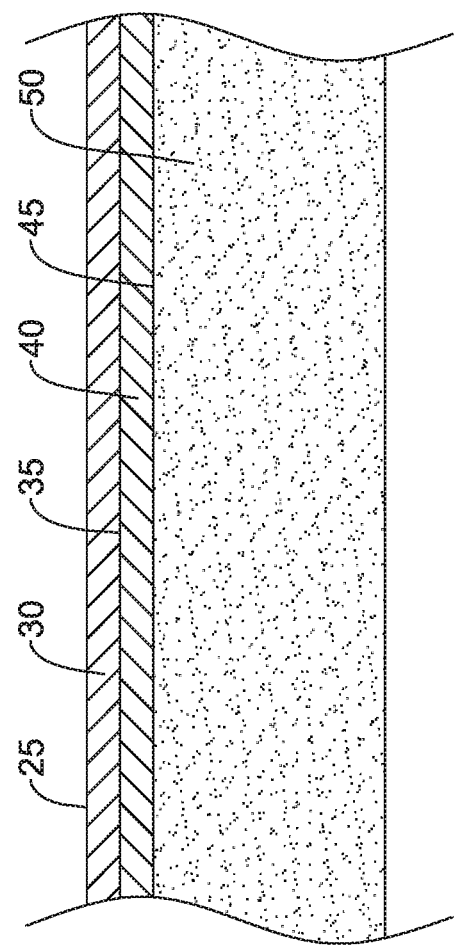
FIG. 3 is an enlarged cross-section of a portion of a cushion as described herein.

The inner polymeric coating layer 40 may surround or cover at least a portion of the inner polymeric foam core 50. For example, the inner polymeric coating layer 40 may be juxtaposed with the polymeric foam core 50 and thus provide an interface 45 between the inner polymeric coating layer 40 and the polymeric foam core 50. The inner polymeric coating layer 40 may be bonded (e.g., chemically bonded, mechanically bonded, adhesively bonded) to the polymeric foam core 50 throughout the interface 45 between the inner polymeric coating layer 40 and the polymeric foam core 50 as shown in FIG. 3. In some instances, a chemical bond between the inner polymeric coating layer 40 and the polymeric foam core 50 may be formed during the molding process for forming the cushion 20, as described further herein.

The outer polymeric coating layer 30 may surround or cover at least a portion of the inner polymeric coating layer 40. For example, the outer polymeric coating layer 30 may be juxtaposed with the inner polymeric coating layer 40, and thus provide an interface 35 between the outer polymeric coating layer 30 and the inner polymeric coating layer 40. The outer polymeric coating layer 30 may be bonded (e.g., chemically bonded, mechanically bonded, adhesively bonded) to the inner polymeric coating layer 40 throughout the interface 35 between the inner polymeric coating layer 40 and the outer polymeric coating layer 30. In some instances, a chemical bond between the inner polymeric coating layer 40 and the outer polymeric coating layer 30 may be formed during the molding process for forming the cushion 20, as described further herein.

In some instances, as a result of the molding process for forming the cushion 20, diffusion of the polymeric foam material of the core 50 into the inner coating layer 40, or diffusion of the polymeric foam material of the core 50 into the inner and outer coating layers 40, 30, may occur. For example, polymeric foam material forming the core 50 may diffuse across the interface 45 and into the inner polymeric coating layer 40 in some instances. In other instances, polymeric foam material forming the core 50 may diffuse into the outer polymeric coating layer 30 across the interface 35, as well as across the interface 45 and into the inner polymeric coating layer 40.

In some instances, the mold in which the cushion 20 is molded may include a textured cavity which may form a corresponding textured outer surface 25 on the cushion 20. Thus, the outer surface 25 of the outer coating layer 30 may have a visually identifiable texture thereon imparted by the mold. The visually discernable texture may provide preferential creasing and/or dissipation of wrinkling when the cushion 20 is subjected to compression and deformation, as well as providing the cushion 20 with an aesthetically pleasing feel and appearance.

Outer Coating Layer

The outer coating layer 30 may be present to provide the cushion 20 with enhanced abrasion resistance and/or chemical resistance while having an aesthetically pleasing feel and appearance. The outer coating layer 30 may be a polymeric coating formed of a desired mixture of constituents to provide the desired characteristics for the outer coating layer 30. In some embodiments, the outer coating layer 30 may be an unfoamed polymeric coating distinct from the inner coating layer 40 and the core 50. For example, the outer coating layer 30 may be a urethane based (e.g., polyurethane) polymeric coating, a vinyl based (e.g., polyvinyl chloride) polymeric coating, or an acrylic based polymeric coating. In some embodiments, the outer coating layer 30 may be formed from a mixture of polyurethane dispersions (or polyvinyl chloride dispersions if vinyl based), coalescing solvents, wetting agents, and/or crosslinkers. The outer coating layer 30 may be an aqueous based coating, a solvent based coating, or a solvent-less based coating (e.g., UV cured coating), for example.

Some suitable polyurethane dispersions include: Hauthane HD 4670 and/or Hauthane HD 2024, each available from Hauthaway Corporation, of Lynn, Mass., or NeoRez R-1010, available from DSM NeoResins of Wilmington, Mass. The Hauthane HD 4670 dispersion provides a very soft, flexible urethane coating layer. The Hauthane HD 4670 dispersion may be selected due to its resulting coating layer having a very low elastic modulus and high elongation at break. The Hauthane HD 4670 resulting coating has an elastic modulus of 200 psi at 100% elongation, with an elongate at break of 800%. The Hauthane HD 2024 dispersion provides a soft, tough, and flexible urethane coating having very good abrasion resistance, and may be selected due to its low elastic modulus while still containing good tensile strength and elongation. The Hauthane HD 2024 dispersion provides a coating with an elastic modulus of 480 psi at 100% elongation, 680 psi at 200% elongation and 890 psi at 300% elongation, with an ultimate tensile strength of 4,000 psi and elongation at break of 750%. In addition to providing high tensile strength, the inclusion of Hauthane HD 2024 dispersion may reduce the tackiness and increase chemical resistance of the coating layer. The NeoRez R-1010 polyurethane dispersion may provide a soft feel effect, excellent chemical resistance, and low gloss. The NeoRez R-1010 dispersion may be selected to improve the feel of the coating layer and decrease the gloss level of the coating layer. The outer coating layer 30 may have an elastic modulus of about 500 psi or less, about 400 psi or less, about 300 psi or less, about 250 psi or less, about 200 psi or less, or about 150 psi or less at 100% elongation, for example. The outer coating layer 30 may have an elongation at break of 600% or more, 650% or more, 700% or more, 750% or more, or 800% or more, for example.

Dipropylene n-butyl ether (DPnB) is one suitable coalescing medium. Alternative coalescing media which may alternatively or additionally be used include dipropylene glycol methyl ether (DPM) or propylene glycol methyl ether, as well as other media known to those skilled in the art.

Suitable wetting agents include silicone and non-silicone based chemistries, such as the silicone based wetting agent BYK 348 available from BYK Chemie of Wallingford, Conn. Alternatively or additionally, other silicone surfactants may also be included in the coating mixture, if desired. One suitable non-silicone based wetting agent is Aerosol-OT-75 available from Cytec of West Patterson, N.J.

Suitable crosslinkers may include polymeric carbodiimide based crosslinkers, such as V-02-L2 and E2 available from Nisshinbo/GSI-Exim America of New York, N.Y. Carbodilite V-02-L2, or a similar crosslinker, may be selected to increase the chemical resistance and strength of the coating layer, without significantly hardening the coating layer.

The mixture for the outer coating layer 30 may also include additional additives including a defoamer (e.g., a silicone based defoamer or a non-silicone based defoamer) or anti-foaming agent, such as BYK 028 available from BYK Chemie of Wallingford, Conn. Furthermore, the mixture for the outer coating layer 30 may include a pigment to provide the outer coating layer 30 with a desired coloration. For example, the mixture for the outer coating layer 30 may include a black pigment, for example a carbon black aqueous pigment dispersion, such as UCD 1507Q available from Plasticolors Inc. of Ashtabula, Ohio. However, other pigments may be included, if desired. Other additives include UV stabilizers, antioxidants, fillers, and anti-microbials, for example.

In forming the polymeric mixture for the outer coating layer 30, the polymeric dispersion(s) may be provided in the range of 70 to 80 weight percent of the total formulation, the coalescing media(s) may be provided in the range of 0 to 10 weight percent of the total formulation, the wetting agent(s) may be provided in the range of 0.05 to 0.7 weight percent of the total formulation, and the crosslinker(s) may be provided in the range of 5 to 11 weight percent of the total formulation, or about 5 to 8 weight percent of the total formulation, based on solids of polyurethane present.

One suitable formulation of the outer coating layer 30 is as follows:

| Ingredient | Formulation 1 (Weight %) |
| --- | --- |
| HD 2024[1] | 16.37 |
| HD 4670[2] | 61.36 |
| R-1010[3] | 4.09 |
| DPnB[4] | 1.10 |
| Water | 1.21 |
| V-02-L2[5] | 6.90 |
| BYK 348[6] | 0.70 |
| BYK 028[7] | 0.09 |
| UCD 1507Q[8] | 8.19 |

[1]Hauthane HD-2024 - Hauthaway Corp., Lynn MA
[2]Hauthane HD-4670 - Hauthaway Corp., Lynn MA
[3]NeoRez R-1010 - DSM NeoResins, Wilmington, MA
[4]dipropylene n-butyl ether (DPnB) - Dow Corning Corp., Midland, MI
[5]V-02-L2 - Nisshinbo/GSI-Exim America, New York, NY
[6]BYK 348 - BYK Chemie, Wallingford, CT
[7]BYK 028 - BYK Chemie, Wallingford, CT
[8]UCD 1507Q - Plasticolors Inc., Ashtabula, OH In the formulation above, the Hauthane HD 4670 polyurethane dispersion may be provided in the range of 40-80 weight percent, the Hauthane HD2024 polyurethane dispersion may be provided in the range of 0-70 weight percent, and the NeoRez R-1010 polyurethane dispersion may be provided in the range of 0-50 weight percent of the total formulation.

The thickness of the outer coating layer 30 may be in the range of about 0.5 mils to about 3.0 mils (0.0005 inches to 0.003 inches), about 0.5 mils to about 2.5 mils (0.0005 inches to 0.0025 inches), about 0.5 mils to about 2.0 mils (0.0005 inches to 0.002 inches), or about 0.5 mils to about 1.5 mils (0.0005 inches to 0.0015 inches) in some instances.

Inner Coating Layer

The inner coating layer 40 may be present to provide the cushion 20 with strength, while providing a high degree of flexibility and suppleness to closely conform around contours and obstructions. The inner coating layer 40 may be a polymeric coating formed of a desired mixture of constituents to provide the desired characteristics for the inner coating layer 40. In some embodiments, the inner coating layer 40 may be an unfoamed polymeric coating distinct from the outer coating layer 30 and the core 50. For example, the inner coating layer 40 may be a urethane based (e.g., polyurethane) polymeric coating, a vinyl based (e.g., polyvinyl chloride) polymeric coating, or an acrylic based polymeric coating. In other embodiments, the inner coating layer 40 may be a nitrile based coating, such as a high acrylonitrile based nitrile rubber coating or a medium acrylonitrile based nitrile rubber coating. In some instances a high acrylonitrile based nitrile rubber coating may be selected due, at least in part, to its chemical and moisture resistance and high mechanical strength. In some embodiments, the inner coating layer 40 may be formed of a mixture of polyurethane dispersions (or polyvinyl chloride dispersions if vinyl based), coalescing solvents, wetting agents, and/or crosslinkers. The inner coating layer 40 may be an aqueous based coating, a solvent based coating, or a solventless based coating (e.g., UV cured coating), for example.

One suitable high acrylonitrile based nitrile rubber coating is based on the 1571X12 Nychem™ emulsion available from Emerald Performance Materials, of Akron, Ohio. This emulsion shows high chemical and moisture resistance as well as high mechanical strength.

Some suitable polyurethane dispersions include: Hauthane HD 4670 and/or Hauthane HD 2024, each available from Hauthaway Corporation, of Lynn, Mass. The Hauthane HD 4670 dispersion provides a very soft, flexible urethane coating layer. The Hauthane HD 4670 dispersion may be selected due to its very low elastic modulus and elongation at break. The Hauthane HD 4670 resulting coating has an elastic modulus of 200 psi at 100% elongation, with an elongate at break of 800%. The Hauthane HD 2024 dispersion provides a soft, tough, and flexible urethane coating having very good abrasion resistance, and may be selected due to its low elastic modulus while still containing good tensile strength and elongation. The Hauthane HD 2024 dispersion provides a coating with an elastic modulus of 480 psi at 100% elongation, 680 psi at 200% elongation and 890 psi at 300% elongation, with an ultimate tensile strength of 4,000 psi and elongation at break of 750%. In addition to providing high tensile strength, the inclusion of Hauthane HD 2024 dispersion may reduce the tackiness and increase chemical resistance of the coating layer. The inner coating layer 40 may have an elastic modulus of about 400 psi or less, about 300 psi or less, about 250 psi or less, or about 200 psi or less at 100% elongation, for example. The inner coating layer 40 may have an elongation at break of 500% or more, 600% or more, 700% or more, 750% or more, or 800% or more, for example.

The inner coating layer 40 may also include an aromatic polyurethane dispersion (PUD) to increase the bonding between the foam core 50 and the polymeric coating. For example, the inner coating layer 40 may include a blend, such as a 50:50 blend based on total weight percent of the dispersions in the formulation, of an aromatic polyurethane dispersion and the Hauthane HD 4670 dispersion. One suitable aromatic polyurethane dispersion is PU-444 available from Picassian Polymers, of Peabody Mass. PU-444 exhibits excellent adhesion to a wide variety of substrates. The polymer chains of the PU-444 aromatic polyurethane dispersion break down when exposed to light, thus the outer coating layer 30 may shield the PU-444 in the inner coating layer 40 from light to prevent breakdown of the polymer chains.

Dipropylene n-butyl ether (DPnB) is one suitable coalescing medium. Alternative coalescing media which may alternatively or additionally be used include dipropylene glycol methyl ether (DPM) or propylene glycol methyl ether, as well as other media known to those skilled in the art.

Suitable wetting agents include silicone and non-silicone based chemistries, such as the silicone based wetting agent BYK 348 available from BYK Chemie of Wallingford, Conn. Alternatively or additionally, other silicone surfactants may also be included in the coating mixture, if desired. One suitable non-silicone based wetting agent is Aerosol-OT-75 available from Cytec of West Patterson, N.J.

Suitable crosslinkers may include polymeric carboniimide based crosslinkers, such as V-02-L2 and E2 available from Nisshinbo/GSI-Exim America of New York, N.Y. Carbodilite E2, or a similar crosslinker, may be selected to increase the chemical resistance and strength of the coating layer, while reducing the tacky nature of the coating layer at elevated temperatures. The mixture for the inner coating layer 40 may also include additional additives including a defoamer (e.g., a silicone based defoamer or a non-silicone based defoamer) or anti-foaming agent, such as BYK 028 available from BYK Chemie of Wallingford, Conn. Furthermore, the mixture for the inner coating layer 40 may include a pigment to provide the inner coating layer 40 with a desired coloration. For example, the mixture for the inner coating layer 40 may include a black pigment, for example a carbon black aqueous pigment dispersion, such as UCD 1507Q available from Plasticolors Inc. of Ashtabula, Ohio. However, other pigments may be included, if desired.

In forming the polymeric mixture for the inner coating layer 40, the polymeric dispersion(s) may be provided in the range of 80 to 98 weight percent of the total formulation, the coalescing solvent(s) may be provided in the range of 0 to 10 weight percent of the total formulation, the wetting agent(s) may be provided in the range of 0.05 to 0.8 weight percent of the total formulation, and the crosslinker(s) may be provided in the range of 0 to 7 weight percent of the total formulation, or about 3 to 4 weight percent of the total formulation, based on solids of polyurethane present.

One suitable formulation of the inner coating layer 40 is as follows:

| Ingredient | Formulation 1 (Weight %) |
| --- | --- |
| HD 4670[1] | 89.27 |
| DPnB[2] | 1.18 |
| Water | 1.29 |
| E2[3] | 2.95 |
| BYK 348[4] | 0.76 |
| BYK 028[5] | 0.10 |
| UCD 1507Q[6] | 4.46 |

[1]Hauthane HE-4670 - Hauthaway Corp., Lynn MA
[2]dipropylene n-butyl ether (DPnB) - Dow Corning Corp., Midland, MI
[3]E2 - Nisshinbo/GSI-Exim America, New York, NY
[4]BYK 348 - BYK Chemie, Wallingford, CT
[5]BYK 028 - BYK Chemie, Wallingford, CT
[6]UCD 1507Q - Plasticolors, Ashtabula, OH In the formulation above, the Hauthane HD 4670 polyurethane dispersion may be provided in the range of 50-98 weight percent, and in some instances 0-50 weight percent of the Hauthane HD2024 polyurethane dispersion may be added to the total formulation.

Another suitable formulation of the inner coating layer 40 is as follows:

| Ingredient | Formulation 2 (Weight %) |
|---|---|
| 1571X12[1] | 99 |
| Synperonic 13/6[2] | 0.4 |
| Aerosol OT75[3] | 0.4 |
| Chartwell B 515.71W[4] | 0.2 |

[1]Nychem ™ 1571X12 - Emerald Performance Materials, Akron, OH
[2]Synperonic 13/6 - Croda, Edison, NJ
[3]Aerosol OT75 - Cytec, West Patterson, NJ
[4]Chartwell B 515.71W - Chartwell International, Inc., North Attleborough, MA The thickness of the inner coating layer 40 may be in the range of about 0.5 mils to about 3.0 mils (0.0005 inches to 0.003 inches), about 0.5 mils to about 2.5 mils (0.0005 inches to 0.0025 inches), about 0.5 mils to about 2.0 mils (0.0005 inches to 0.002 inches), or about 0.5 mils to about 1.5 mils (0.0005 inches to 0.0015 inches) in some instances.

The compositions for the inner polymeric coating layer 40 and the outer polymeric coating layer 30 may be chosen such that the inner polymeric coating layer 40 is less crosslinked than the outer coating layer 30. Although less crosslinked than the outer coating layer 30, the inner polymeric coating layer 40 may have a chemical composition similar to the chemical composition of the outer polymeric coating layer 30. Accordingly, the inner polymeric coating layer 40 may include a different crosslinker and/or a smaller quantity (e.g., weight percent) of a crosslinker than the outer polymeric coating layer 30 to provide the varied crosslinking between the outer and inner coating layers 30, 40. Furthermore, the outer polymeric coating layer 30 and the inner polymer coating layer 40 may each include functional groups that cause the layers to adhere together, whether by chemical or mechanical bonds or forces.

Moreover, the inner polymeric coating layer 40 may be chemically compatible with the outer polymeric coating layer 30. For instance, the inner polymeric coating layer 40 and the outer polymeric coating layer 30 may both be formed of polymeric materials of a chemically similar family of polymers (e.g., urethanes, vinyls). In some instances, the inner polymeric coating layer 40 and the outer polymeric coating layer 30 may both be polyurethane based polymers. For example, the outer polymeric coating layer 30 may be formed of a mixture of two or more polyurethane dispersions, while the inner polymeric coating layer 40 may be formed of at least one of the polyurethane dispersions of the outer polymeric coating layer 30. In some instances, the polyurethane dispersion included in both the outer polymeric coating layer 30 and the inner polymeric coating layer 40 may be provided in a greater weight percent in the inner polymeric coating layer 40 than in the outer polymeric coating layer 30. In other instances, the inner polymeric coating layer 40 may be an acrylonitrile based nitrile rubber, such as a high acrylonitrile based nitrile rubber coating or a medium acrylonitrile based nitrile rubber coating, and the outer polymeric coating layer 30 may be formed of a polyurethane dispersion or a mixture of two or more polyurethane dispersions.

Foam Core

The polymeric foam material forming the core 50 may be formed in various manners. For instance, the polymeric foam material forming the core 50 may be formed by combining an isocyanate with a polyol, blowing agent, and catalyst mixture to react and form a polyurethane foam or combining a reactive system of another polymeric mixture with a blowing agent to form a polymeric foam material. In other instances, the polymeric foam material forming the core 50 may be a vinyl based (e.g., polyvinyl chloride) polymeric foam material.

Although other compositions are contemplated, in some instances the polymeric foam material may be an open cell polyurethane foam made by reacting an isocyanate, such as the Suprasec 2527 prepolymer supplied by Huntsman Corporation of Salt Lake City, Utah, with a polyol mixture, such as a mixture of one or more of polyols listed below, in the presence of a catalyst, such as Niax A-1 available from Momentive Performance Materials of Columbus, Ohio, Dabco BL-11 available from Air Products of Allentown, Pa., and/or Dabco 33-LV available from Air Products of Allentown, Pa. Niax A-1 contains 70% bis(2-dimethylaminoethyl) ether. Dabco 33-LV is a solution of 33% triethylenediamine and 67% dipropylene glycol.

The polyol mixture may include one or more polyether polyols, such as glycerine and propylene oxide based polyether polyol triols, and/or one or more bio-based polyols. Some suitable polyether polyols include: Carpol GP-240, a 700 molecular weight glycerine and propylene oxide based polyether polyol triol, available from Carpenter Company of Richmond, Va.; Carpol GP-3008, a 3000 molecular weight glycerine and propylene oxide based polyether polyol triol with 8% ethylene oxide located internally, available from Carpenter Company of Richmond, Va.; Carpol GP-6515, a 6000 molecular weight glycerine and propylene oxide based polyether polyol triol with 15% ethylene oxide located internally, available from Carpenter Company of Richmond, Va.; Carpol GP-5171, a reactive 5000 molecular weight glycerine and propylene oxide based polyether polyol triol with 71% ethylene oxide capacity, available from Carpenter Company of Richmond, Va.; BiOH 5400, a bio-based polyol for use in polyurethanes having a molecular weight of 1445, available from Cargill, Inc. of Minneapolis, Minn.; and Duranol™ T5652, a polycarbonate diol, available from Asahi Kasei Chemicals Corp. of Tokyo, Japan.

The composition of the polymeric foam material forming the core 50 may also include one or more surfactants (e.g., wetting agents, foam stabilizing agents, etc.) or other additives. For example, the composition may include a foam stabilizing agent, such as Dabco DC-198 available from Air Products of Allentown, Pa. and/or Dabco DC-5982 also available from Air Products of Allentown, Pa.; a stabilizing additive, such as Geolite Modifier 210 available from Momentive Performance Materials of Columbus, Ohio to produce foam at a lower index; and/or an additive to strengthen and improve the tensile/elongation/tear properties of the foam, such as Niax DP-1022 available from Momentive Performance Materials of Columbus, Ohio.

In some instances, a filler material, such as a short acrylic fiber filler may be incorporated into the foam to provide added strength, toughness and/or abrasive resistance.

In some instances, a gel, such as a polyurethane gel, could be incorporated into the foam to provide more uniform pressure and improved heat capacity of the foam. The gel may be added to the foam as a feed stream into the mix head for the polymeric foam composition, or added in another way, if desired.

Some suitable formulations of the polymeric foam composition forming the core 50 are as follows:

| Ingredient | Formulation 1 (Weight %) | Formulation 2 (Weight %) | Formulation 3 (Weight %) | Formulation 4 (Weight %) | Formulation 5 (Weight %) |
|---|---|---|---|---|---|
| GP-240[1] | 29.76 | — | 31.44 | — | — |
| GP-3008[2] | 12.89 | 7.71 | 3.51 | — | — |
| GP-6515[3] | — | — | — | — | 0.22 |
| GP-5171[4] | 18.6 | 31.84 | 26.57 | 29.04 | 28.48 |
| BiOH 5400[5] | — | 23.26 | — | 38.11 | 37.38 |
| T5652[6] | — | — | — | — | 4.45 |
| Niax DP1022[7] | — | 1.29 | — | 0.95 | 0.93 |
| Geolite 210[8] | 5.53 | 5.55 | 4.65 | 4.24 | 4.16 |
| Dabco DC-198[9] | 0.25 | 0.75 | 0.75 | 0.68 | 0.45 |
| Dabco DC-5982[10] | — | 0.5 | — | 0.45 | 0.45 |
| Dabco 33-LV[11] | 0.37 | 0.37 | 0.37 | 0.34 | 0.33 |
| Niax A-1[12] | 0.12 | 0.12 | 0.12 | 0.11 | 0.11 |
| Suprasec 2527[13] | 32.48 | 28.61 | 32.59 | 26.08 | 23.04 |

[1]Carpol GP-240 - Carpenter Company, Richmond, VA
[2]Carpol GP-3008 - Carpenter Company, Richmond, VA
[3]Carpol GP-6515 - Carpenter Company, Richmond, VA
[4]Carpol GP-5171 - Carpenter Company, Richmond, VA
[5]BiOH 5400 - Cargill Inc., Minneapolis, MN
[6]Duranol T5652 - Asahi Kasei Chemicals Corp., Tokyo, Japan
[7]Niax DP-1022 - Momentive Performance Materials, Columbus, OH
[8]Geolite Modifier 210 - Momentive Performance Materials, Columbus, OH
[9]Dabco DC-198 - Air Products, Allentown, PA
[10]Dabco DC-5982 - Air Products, Allentown, PA
[11]Dabco 33-LV - Air Products, Allentown, PA
[12]Niax A-1 - Momentive Performance Materials, Columbus, OH
[13]Suprasec 2527 - Huntsman Corporation, Salt Lake City, UT The follow table provides some suitable ranges for ingredients of a polymeric foam material which may be used to form the core 50 with satisfactory resulting properties.

| Ingredient | Formulation (Weight %) |
|---|---|
| GP-5171[3] | 23.1-31.8 |
| BiOH 5400[4] | 28.8-40.9 |
| Niax DP1022[5] | 0.4-1.3 |
| Geolite 210[6] | 4.15-5.5 |
| Dabco DC-198[7] | 0.25-0.75 |
| Dabco DC-5982[8] | 0-0.5 |
| Dabco 33-LV[9] | 0.34-0.37 |
| Niax A-1[10] | 0.11-0.12 |
| Suprasec 2527[11] | 23.0-32.6 |

It is noted that with the above provided ranges of ingredients of a foam material formulation, the ratio of equivalent weight of GP-5171 to the equivalent weight of BiOH 5400 be in the range of 0.13 to 0.30.

The polymeric foam material forming the foam core 50 may be a slow recovery, viscoelastic foam, having a softness uncharacteristic of other slow recovery, viscoelastic foams, which are stiffer. Typically, the glass transition temperature, Tg, of viscoelastic foams is about 0° C. However, the polymeric foam material for the foam core 50 described herein at Formulation 4 has a first Tg at about −45° C. and a second Tg at about −25° to −30° C. or about −20° to −30° C. The lower glass transition temperatures of the foams formed in accordance with this disclosure allow the foams to feel softer and retain that softness to a lower operating temperature compared to other foams having equal densities. In some instances, the polymeric foam core 50 may have a first glass transition temperature of less than 0° C. and a second glass transition temperature of about −25° or less. In some instances, the polymeric foam core 50 may have a first glass transition temperature of less than −10° C. and a second glass transition temperature of about −25° or less, a first glass transition temperature of less than −20° C. and a second glass transition temperature of about −25° or less, a first glass transition temperature of less than −30° C. and a second glass transition temperature of about −25° or less, or a first glass transition temperature of less than −40° C. and a second glass transition temperature of about −25° or less or about −20° or less.

Manufacturing Process

The cushion 20 may be formed according to the following process. A mold may be provided having a cavity therein shaped in the desired shape of the cushion 20. In some instances the surface of the mold defining the cavity may be a textured surface having a desired texture for imparting on the outer surface of the cushion 20. The mold may be formed of silicone, metal, polymer or other material as desired. The mold may initially be heated to an elevated temperature in the range of about 20° C. to about 90° C., in the range of about 50° C. to about 90° C., or about 70° C., for example. While at the elevated temperature, the outer coating layer 30 may be applied to the surface of the cavity of the mold in liquid form and then allowed to dry. In some instances, the outer coating layer 30 may be sprayed, poured, painted or otherwise applied into the mold. In some instances, the outer coating layer 30 may dry almost instantaneously as the elevated temperature of the mold tends to evaporate the solvent (e.g., water) in the outer coating layer 30, although the outer coating layer 30 may not yet be fully cured at this stage.

Thereafter, the inner coating layer 40 may be applied in a liquid form on the previously applied outer coating layer 30 in the cavity of the mold. In some instances, the inner coating layer 40 may be sprayed, poured, painted, or otherwise applied into the mold over the outer coating layer 30. The inner coating layer 40 may then be allowed to dry, which in some instances may occur almost instantaneously at the elevated temperature of the mold, as the solvent (e.g. water) in the inner coating layer 40 evaporates. Similar to the outer coating layer 30, the inner coating layer 40 may not yet be fully cured at this stage.

With the outer and inner coating layers 30, 40 applied to the mold and allowed to dry, the foam composition is then poured in the cavity of the mold and the cavity is capped with a mounting plate which may be bonded to the inner coating layer 40. In some instances, the mounting plate may be secured with an adhesive. The mold may be vented to atmospheric pressure during the foaming process. The foam composition undergoes a foaming chemical reaction to form a polymeric foam core 50 filling the volume of the cavity in the mold. In some instances, the foam composition may be controllably metered into the mold cavity such that when the foam composition foams, the quantity of foam composition poured into the cavity forms a foam core 50 having a volume substantially filling the cavity without appreciably exceeding the volume of the cavity. In some instances, the foaming reaction may be momentarily delayed (e.g., for about 30 seconds), for example by the inclusion of a blocking acid in the foam composition, to facilitate metering the foam composition into the mold. One suitable blocking agent is Dabco BA100, available from Air Products of Allentown, Pa.

The mold and foamed core (with inner and outer coating layers applied thereto) may then be placed in an oven and heated to an elevated temperature of about 70° C. to about 85° C., or up to 120° C. in some instances, for a duration of time, such as for about 10 to 60 minutes, to allow the foamed core 50, as well as the outer and inner coating layers 30, 40, to cure. Thereafter, the mold may be removed from the oven and allowed to cool, prior to removing the formed cushion 20 (i.e., the foamed core, and inner and outer coating layers) from the cavity of the mold. The formed foam pad or core 50, with the outer and inner coating layers 30, 40 bonded thereto, may be removed from the mold, and in instances in which the surface of the cavity is textured, the outer coating layer 30 may have a visually identifiable texture thereon imparted by the mold. The visually discernable texture may provide preferential creasing and/or dissipation of wrinkling when the cushion 20 is subjected to compression and deformation, as well as providing the cushion 20 with an aesthetically pleasing feel and appearance.

Indentation Test

In order to quantitatively evaluate the conforming characteristics of a cushion as described herein to commercially available competitive headphone cushions, a testing apparatus and associated testing method were created in house at Hearing Components, Inc. of Oakdale, Minn., the assignee of the current application. The associated test will be called the Indentation Test, herein. The object of the Indentation Test is to indirectly measure the gap of the cushion created when a bar is pressed into the cushion to a specified depth. This test is intended to simulate the ability of the cushion to conform when engaging the bow of a wearer's eyeglasses. The test is conducted in a controlled environment at ambient temperature (21° C.) and 40% relative humidity.

Figure 4:
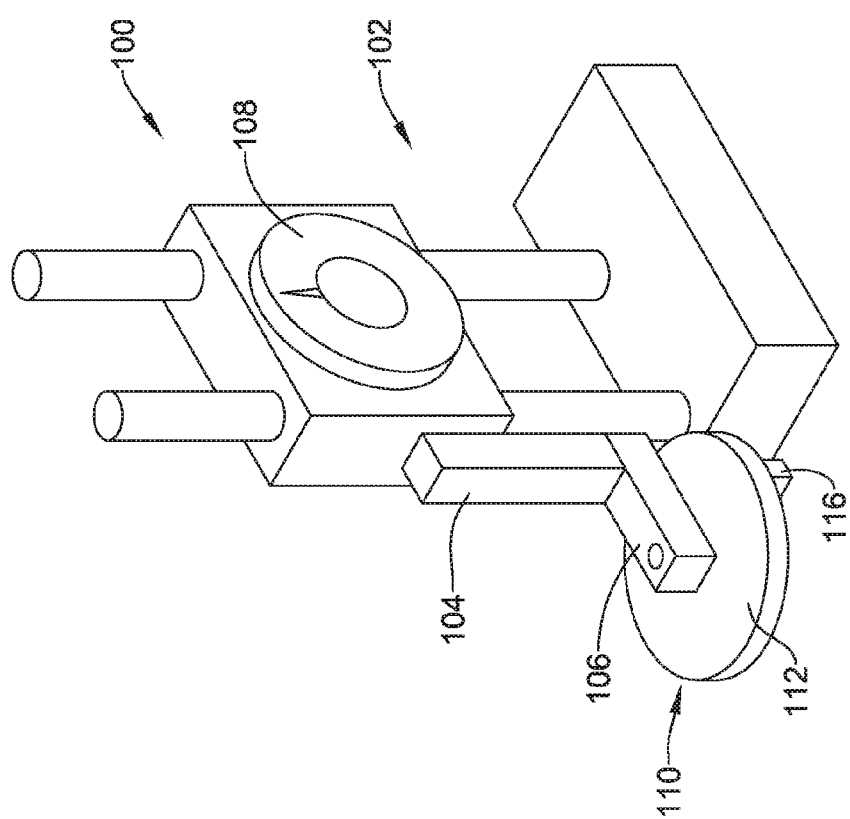
FIG. 4 is a perspective view of an exemplary testing apparatus for use in the Indentation Test as described herein.

As shown in FIG. 4, the testing apparatus 100 includes a height gauge stand 102 and a test fixture 110 attached to the arm 104 of the height gauge stand 102, such as with a mounting bracket 106. The height gauge stand 102 also includes a gauge 108, or other readout, for indexing the measured height from the height gauge stand 102.

Figure 5:
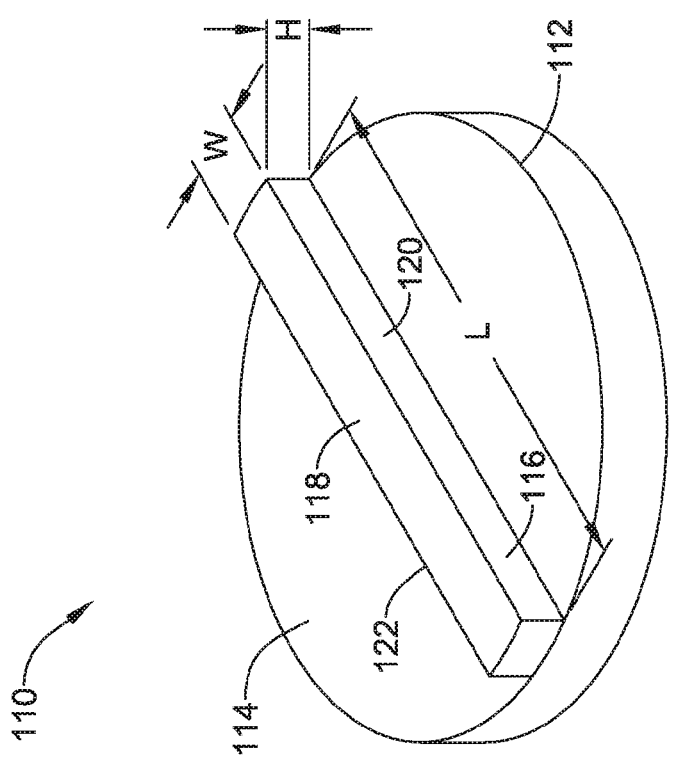
FIG. 5 is a perspective view of the testing fixture of the testing apparatus of FIG. 4 for use in the Indentation Test as described herein.

The test fixture 110 is further illustrated in FIG. 5. The test fixture 110 includes a plate 112, such as a clear tempered glass purchased from McMaster, having a flat, planar lower surface 114. An elongate bar 116 is mounted to the plate 112 and extends from the lower surface 114 of the plate 112. The bar 116 has a flat, planar lower surface 118, parallel to the lower surface 114 of the plate 112, and two parallel side surfaces 120, 122, extending perpendicular to both the lower surface 114 of the plate 112 and the lower surface 118 of the bar 116. The bar 116 has a length L sufficient to extend across a cushion (i.e., 3 inches), a height H of 0.125 inches measured between the lower surface 114 of the plate 112 and the lower surface 118 of the bar 116, and a width W of 0.195 inches measured between the parallel side surfaces 120, 122.

Figure 6:
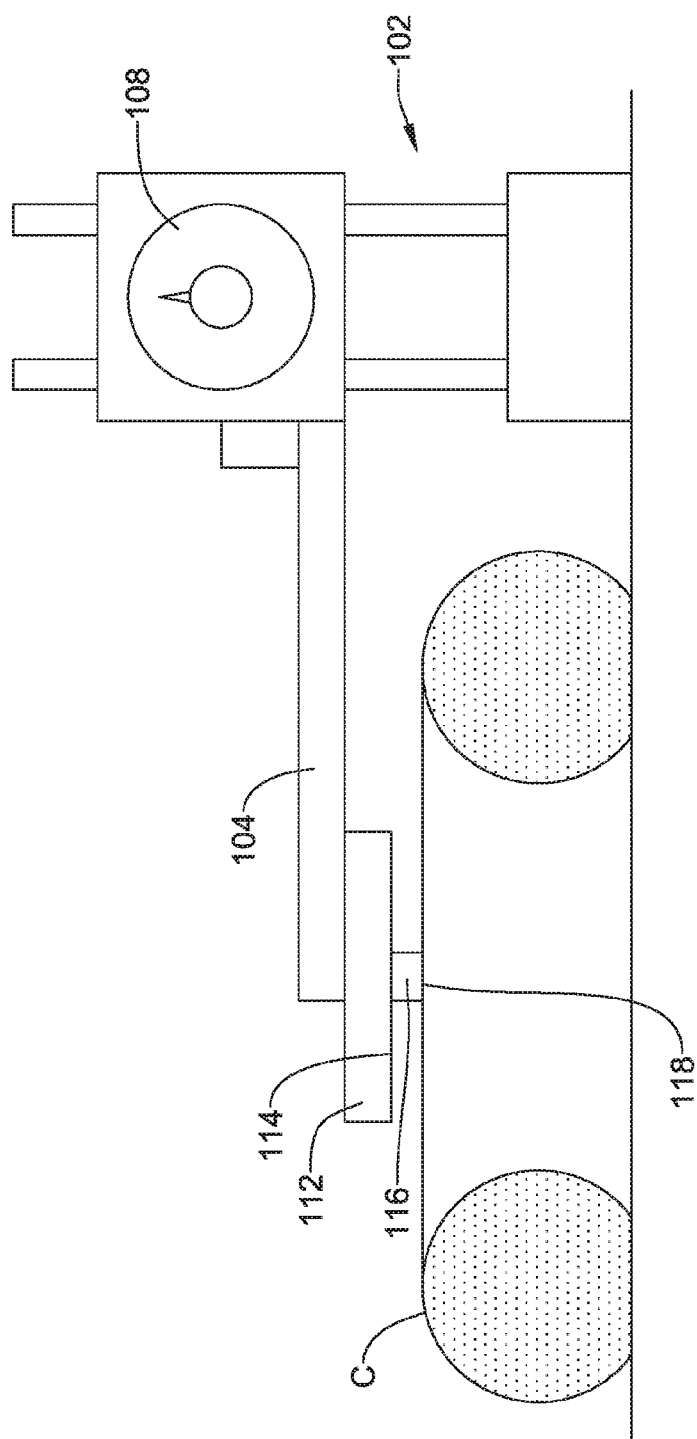
FIG. 6 is a side cross-sectional view of the testing fixture initially contacting a cushion in accordance with the Indentation Test as described herein.
Figure 7:
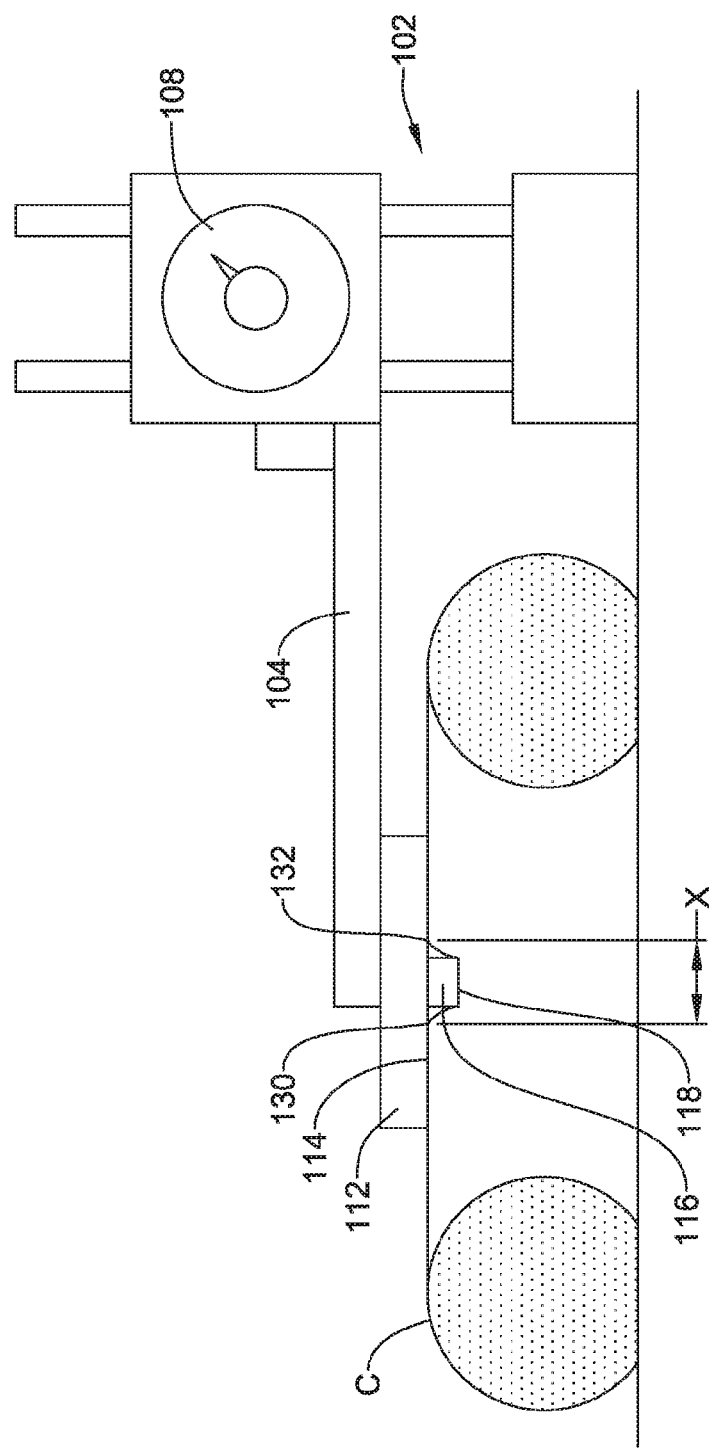
FIG. 7 is a side cross-sectional view of the testing fixture pressed into a cushion a specified amount in accordance with the Indentation Test as described herein.

The test fixture 110 is mounted to the height gauge stand 102 and the lower surface 114 of the plate 112 and the lower surface 118 of the bar 116 are coated with talc powder, or other visually discernable substance. The talc powder can be applied to the lower surfaces 114, 118 with a small sponge, or other applicator. The test cushion C is then placed on a rigid, flat surface (e.g., a table top, or bench) below the test fixture 110, with the lower surface 114 of the plate 112 and the lower surface 118 of the bar 116 facing the cushion C. The test fixture 110 is then lowered toward the cushion C until the lower surface 118 of the bar 116 first initiates contact with the cushion C, as shown in FIG. 6. At the point where the lower surface 118 of the bar 116 initially contacts the cushion C, the gauge 108 of the height gauge stand 102 is zeroed out. With the gauge 108 zeroed out, the test fixture 110 is lowered 0.375 inches onto the cushion C, as shown in FIG. 7. As the test fixture 110 is lowered onto the cushion C, the bar 116 is pushed into the cushion C to deform the cushion C around the bar 116 and the lower surface 114 of the plate 112 is pressed against the upper surface of the cushion C. As shown in FIG. 7, when the cushion C is deformed around the bar 116, a gap X is created where the cushion C is held away from the lower surface 114 of the plate 112. The gap X is the distance between the points 130, 132 on either side of the bar 116 where the cushion C deviates from the lower surface 114 of the plate 112 to deflect around the protruding bar 116. The test fixture 110 is held at this position (lowered 0.375 inches from initial contact of the bar 116 with the cushion C) for 5 seconds, and then the test fixture 110 is lifted off the cushion C. The cushion C is removed from the base and the gap X between the deviation points 130, 132 is visually retained on the cushion C due to the talc powder transferred to the cushion C from the lower surface 114 of the plate 112. The gap X between the deviation points 130, 132 (other than the portion in contact with the lower surface 118 of the bar 116) is not coated with the talc powder, and thus is visually discernable. This gap X is measured, for example, with a calipers. The measured value is documented with the identifying description (e.g., product name, lot number, etc.) of the tested cushion C, and then the test may be repeated for other test cushions C. As used herein the measured gap X is referred to as the Conformability Gap Value of the cushion C.

Figure 8:
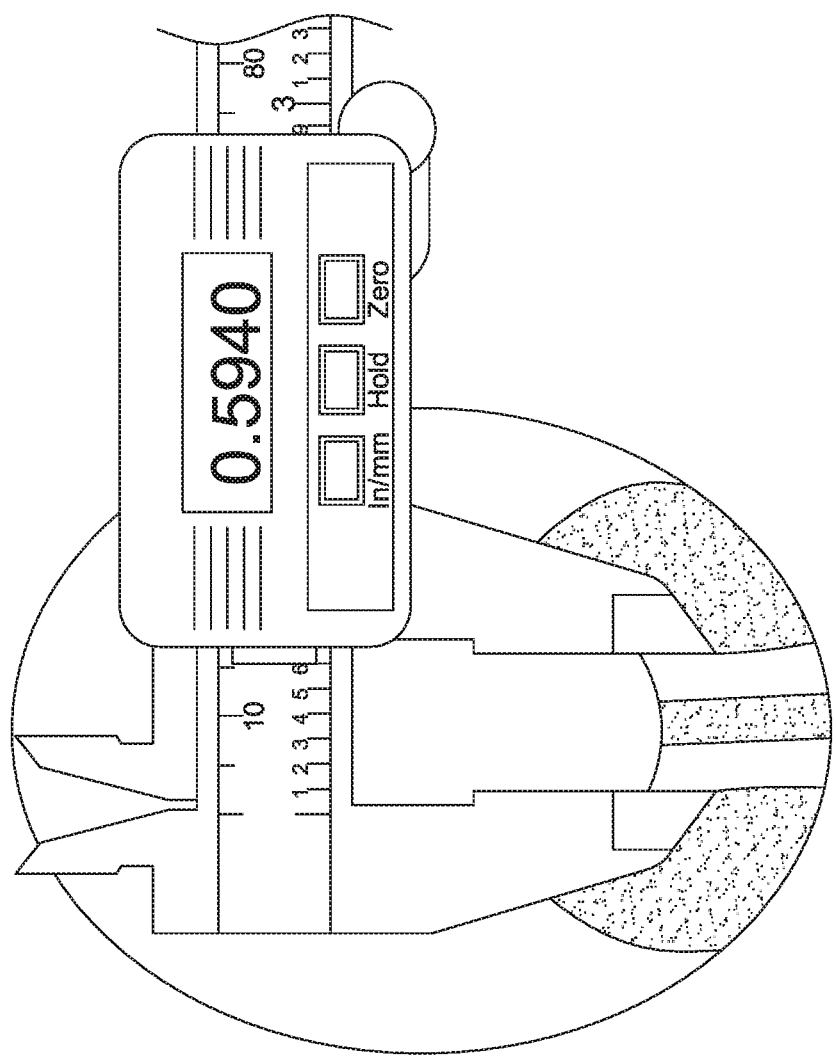
FIG. 8 illustrates the results of the Indentation Test for a sample cushion made in accordance with this disclosure.
Figure 9:
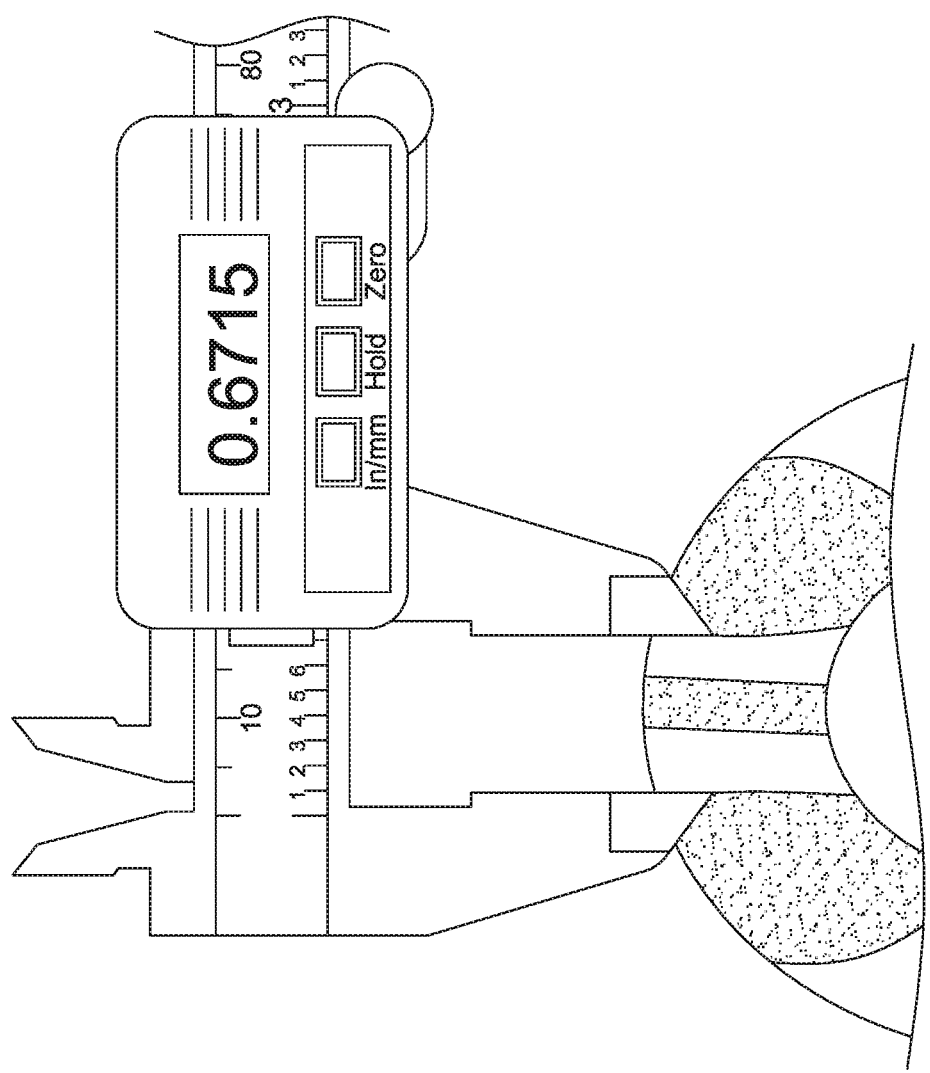
FIG. 9 illustrates the results of the Indentation Test for a cushion from a pair of Bose AE2 headphones.
Figure 10:
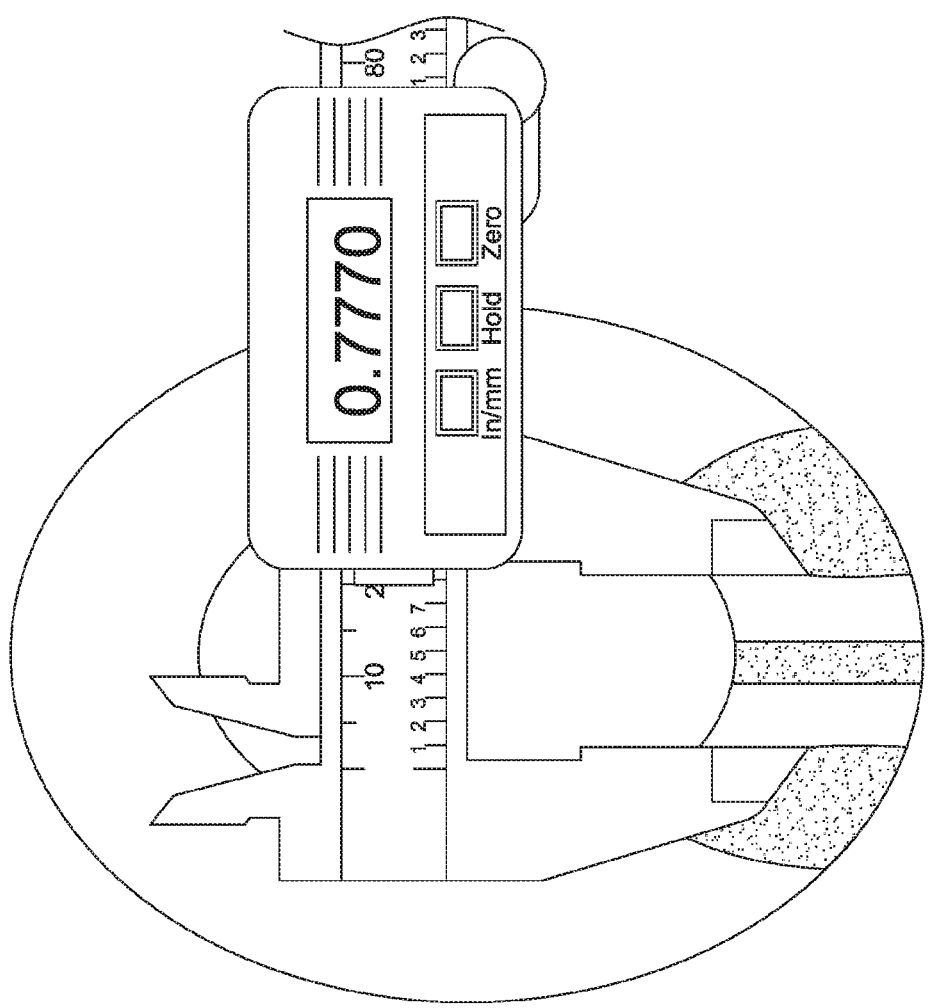
FIG. 10 illustrates the results of the Indentation Test for a cushion from a pair of 3M Peltor headphones.

Below, and at FIGS. 8-10, are test results for a sample cushion made at Hearing Components, Inc. according to this disclosure, compared to two competitor's premium cushions.

| Cushion | Conformability Gap Value (inches) |
|---|---|
| Hearing Components | 0.5940 |
| Bose AE2 | 0.6715 |
| 3M Peltor | 0.7770 |

FIG. 8 shows the gap X and measured value of a sample cushion made at Hearing Components, Inc. having a polymeric foam core made from the formulation 4, above, and the formulations of the inner and outer coating layers, provided above. As can be seen from FIG. 8, the gap X of the sample cushion had a measured value of 0.5940 inches. FIG. 9 shows the gap X and measured value of a cushion of Bose AE2 headphones, available from Bose Corporation. The cushion of the Bose AE2 headphones is a die cut open cell slow recovery foam core encased in a synthetic leather casing. As can be seen from FIG. 9, the gap X of the Bose AE2 cushion had a measured value of 0.6715 inches. FIG. 10 shows the gap X and measured value of a cushion of 3M Peltor headphones, available from 3M Corporation. The cushion of the 3M Peltor headphones is an open cell foam core covered in a vinyl cover. As can be seen from FIG. 10, the gap X of the 3M Peltor cushion had a measured value of 0.7770 inches.

Accordingly, a cushion formed in accordance with this disclosure may have a Conformability Gap Value, according to the Indentation Test specified above, of 0.650 inches or less, 0.635 inches or less, 0.625 inches or less, 0.615 or less, or 0.600 inches or less.

The degree of elasticity and compatibility of the elasticities of the layers of the polymeric coating with the polymeric foam core of the Hearing Components cushion contribute to reduce the Conformability Gap Value, and thus allow the cushion to more closely conform around an object, such as the bar of the test fixture. Thus, the Hearing Components cushion is more effective at sealing the ear canal from unwanted sounds.

Pressure Point Test

In order to quantitatively evaluate the improved comfort provided by the softer feel of a cushion as described herein to commercially available competitive headphone cushions, a testing apparatus and associated testing method were created in house at Hearing Components, Inc. of Oakdale, Minn., the assignee of the current application. The associated test will be called the Pressure Point Test, herein. The object of the Pressure Point Test is to measure the force on a "high point"—a point on the user's head or ear that stands at a higher elevation than the surrounding anatomy. This test is intended to simulate the force exerted on the "high point" of the user's anatomy, and thus the associated comfort experienced by the user when the cushion is pressed against the "high point". The test is conducted in a controlled environment at ambient temperature (21° C.) and 37% relative humidity.

Figure 11:
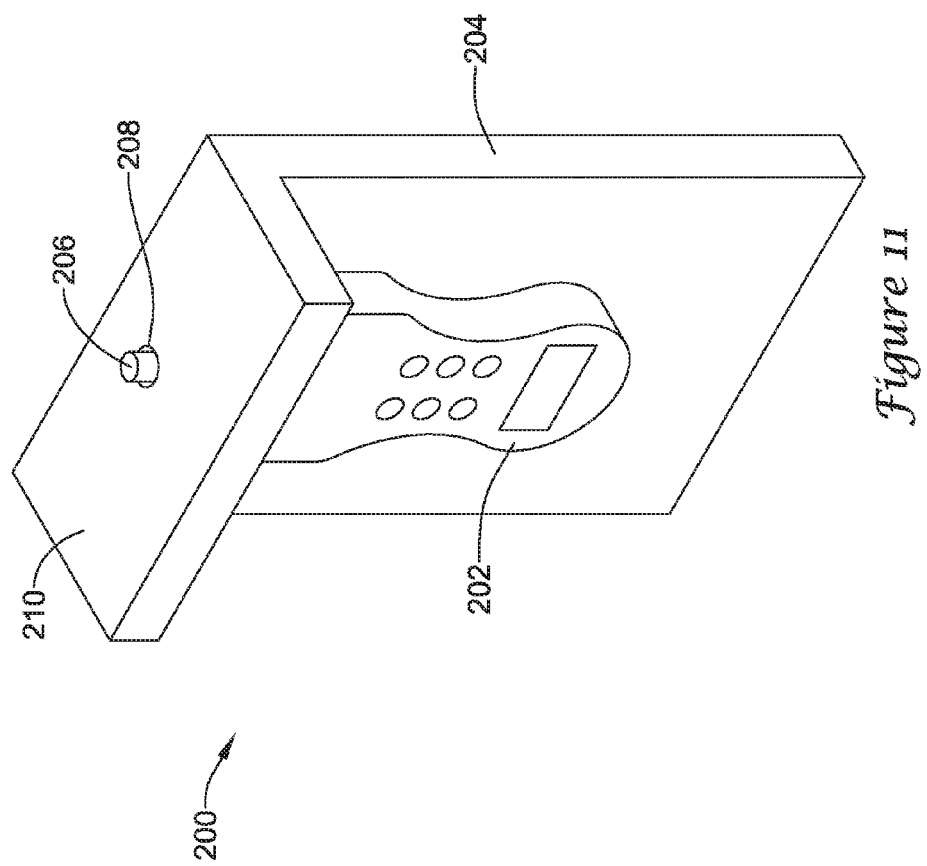
FIG. 11 is a perspective view of an exemplary testing apparatus for use in the Pressure Point Test as described herein.
Figure 12:
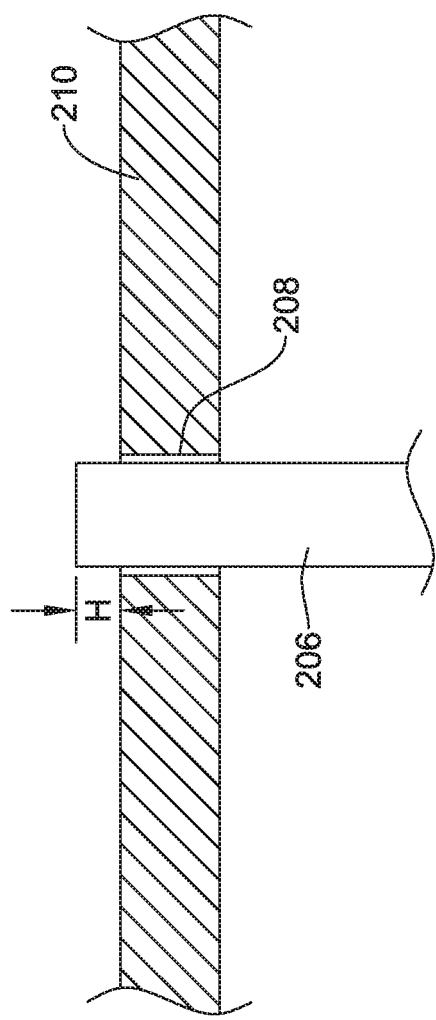
FIG. 12 is a cross-sectional view of a portion of the testing apparatus for use in the Pressure Point Test as described herein.

As shown in FIG. 11, the testing apparatus 200 includes a Dillon load cell 202 mounted to a mounting apparatus 204, with a 6.4 millimeter diameter "button" 206 attached to the end of the Dillion load cell 202 (a Dillon model #AFG 100N load cell was used to acquire the results provided herewith). The button 206 has a flat upper surface. The button 206 and Dillon load cell 202 are mounted to the mounting apparatus 204 such that the button 206 extends through a 9.5 millimeter diameter hole 208 in a flat plate 210 of the mounting apparatus 204. The height H of the portion of the button 206 protruding above the upper surface of the flat plate 210, as shown in FIG. 12, is adjustable by means of slotted holes in the mounting apparatus 204 used to mount the Dillon load cell 202 to the mounting apparatus 204 with threaded fasteners.

Figure 13:
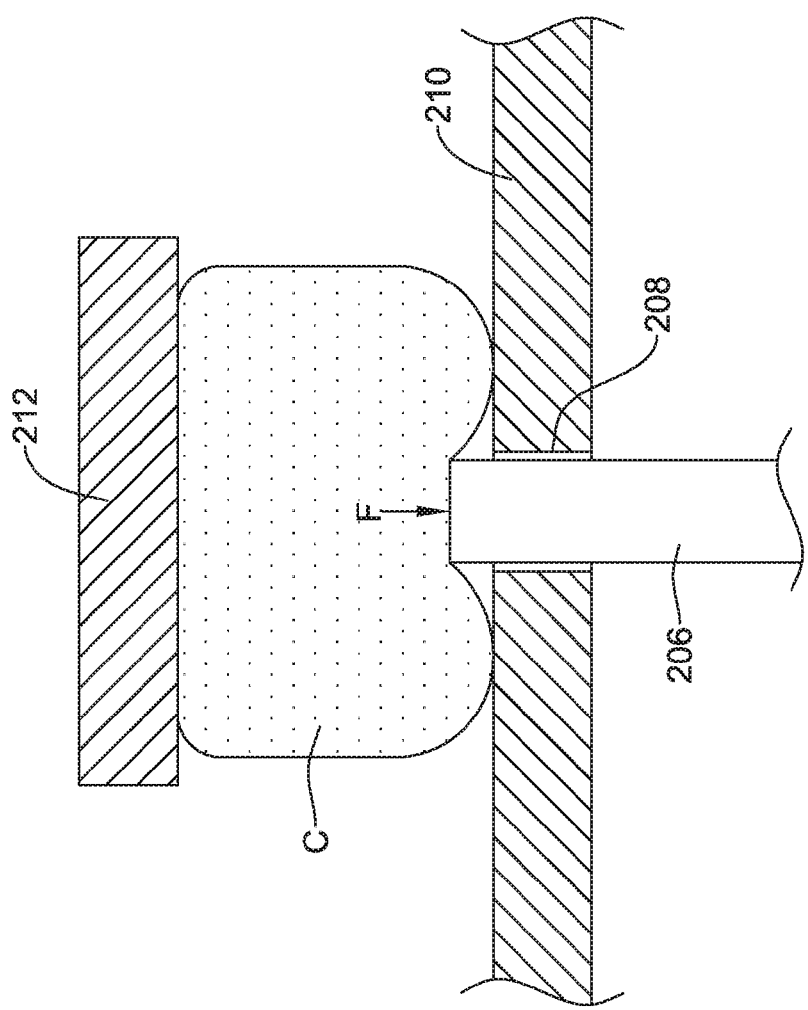
FIG. 13 is a cross-sectional view of a cushion being subjected to the Pressure Point Test as described herein.

The test is carried out by placing a headphone cushion C on the upper surface of the plate 210 so that the button 206 is aligned with the cross-sectional centerline of the cushion C. In other words, the cushion C is placed above the button 206 such that the central axis of the button 206 passes through the center of the cushion C. As shown in FIG. 13, a 310 gram weight 212 is then placed on top of the cushion C, and centered over the button 206. This amount of 310 grams was chosen as this corresponds to the pressure measured to be exerted on the head by each side of the commercially available Bose AE2 headphones. The button 206 is then progressively set at different heights H (i.e., the distance measured between the upper surface of the flat plate 210 and the upper surface of the button 206) protruding above the flat plate 210, and the measured value of the force F exerted between the button 206 and the cushion C at each height H is determined with the Dillon load cell 202. As used herein the measured force F is referred to as the Indentation Force Value of the cushion C and the associated height H of the button 206 above the plate 210 is referred to as the Protrusion Value. The Indentation Force Ratio is the ratio of the Indentation Force Value (Newtons) to the Protrusion Value (millimeters).

Figure 14:
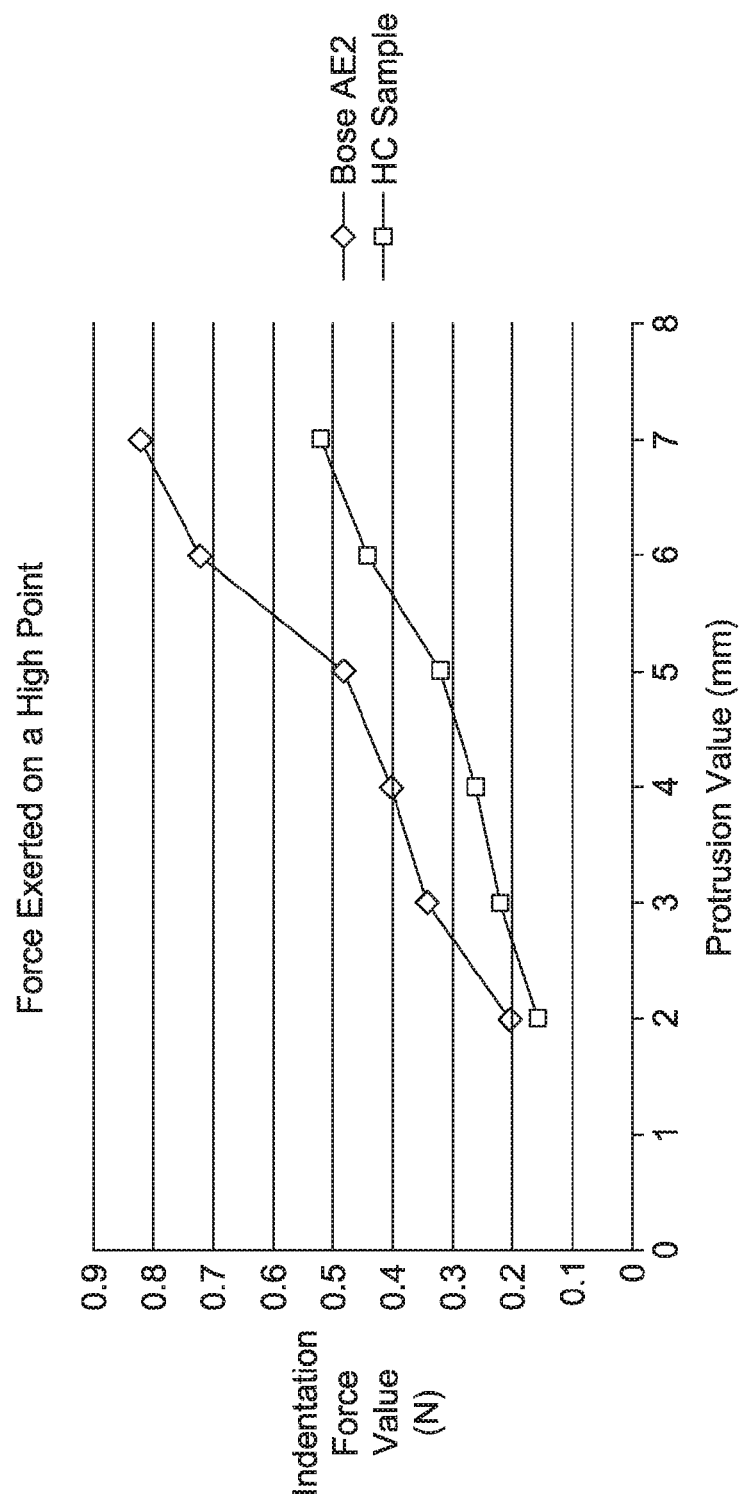
FIG. 14 is a graph illustrating acquired results from cushion samples subjected to the Pressure Point Test.

Below, and in the corresponding graph at FIG. 14 are the test results for a sample cushion made at Hearing Components, Inc. according to this disclosure having a polymeric foam core made from the formulation 4, above, and the formulations of the inner and outer coating layers, provided above, compared to a commercially available cushion of Bose AE2 headphones.

| Protrusion Value | Indentation Force Value (Newtons) | | Indentation Force Ratio | |
|---|---|---|---|---|
| (millimeters) | HC Sample | Bose AE2 | HC Sample | Bose AE2 |
| 2.0 | 0.16 | 0.20 | 0.080 | 0.10 |
| 3.0 | 0.22 | 0.34 | 0.073 | 0.11 |
| 4.0 | 0.26 | 0.40 | 0.065 | 0.10 |
| 5.0 | 0.32 | 0.48 | 0.064 | 0.10 |
| 6.0 | 0.44 | 0.72 | 0.073 | 0.12 |
| 7.0 | 0.52 | 0.82 | 0.074 | 0.12 |

The data above demonstrates that a cushion formed in accordance with this disclosure exerted an average of 33% less force on the "high point" than the Bose AE2 cushion. Accordingly, a cushion formed in accordance with this disclosure may have an Indentation Force Ratio, according to the Indentation Test specified above, of 0.095 or less, 0.090 or less, 0.085 or less, 0.080 or less, 0.075 or less, or 0.070 or less for Protrusion Values of 2.0 to 7.0 millimeters, 2.0 to 6.0 millimeters, 2.0 to 5.0 millimeters, 3.0 to 7.0 millimeters, 3.0 to 6.0 millimeters, 3.0 to 5.0 millimeters, 4.0 to 7.0 millimeters, 4.0 to 6.0 millimeters, or other ranges of Protrusion Values between 2.0 to 7.0 millimeters. The average Indentation Force Ratio of the HC Sample over the Protrusion Value range of 2.0 to 7.0 millimeters was 0.072 [(0.52−0.16)/(7.0−2.0)], whereas the average Indentation Force Ratio of the Bose AE2 sample over the Protrusion Value range of 2.0 to 7.0 millimeters was 0.12 [0.82−0.20)/(7.0−2.0)]. In some instances, the composite cushion formed in accordance with this disclosure may have an average Indentation Force Ratio of 0.10 or less, 0.095 or less, 0.090 or less, 0.085 or less, 0.080 or less, 0.075 or less, or 0.070 or less over a Protrusion Value range of 2.0 to 7.0 millimeters.

The degree of conformability of the Hearing Components cushion contribute to help distribute forces exerted on a user's head by the cushion, and thus allow the cushion to more comfortably conform to the user's anatomy and provide a softer feel against the user's head.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A composite foam cushion for a sound control device to be placed against the head or ear of a user, the composite foam cushion comprising:
   a core formed of a polymeric foam material; and
   a polymeric film overlaying a surface of the core of polymeric foam material, the polymeric film including:
     an inner layer facing the surface of the core of polymeric foam material, the inner layer is formed of a polymeric composition including a crosslinker; and
     an outer layer disposed over the inner layer, the outer layer is formed of a polymeric composition including a crosslinker;
     wherein the inner layer of the film is less crosslinked than the outer layer of the film.

2. The composite foam cushion of claim 1, wherein the polymeric composition of the inner layer of the film is chemically compatible with the polymeric composition of the outer layer of the film.

3. The composite foam cushion of claim 2, wherein the polymeric composition of the inner layer of the film and the polymeric composition of the outer layer of the film are both polyurethane based polymers.

4. The composite foam cushion of claim 1, wherein the crosslinker of the polymeric composition of the outer layer of the film is different than the crosslinker of the polymeric composition of the inner layer of the film.

5. The composite foam cushion of claim 1, wherein the polymeric composition of the inner polymeric coating layer is a high acrylonitrile based nitrile rubber and the polymeric composition of the outer polymeric coating layer is a polyurethane based polymer.

6. The composite foam cushion of claim 1, wherein the core of polymeric foam material has a first glass transition temperature of about −40° C. or less.

7. The composite foam cushion of claim 6, wherein the core of polymeric foam material has a second glass transition temperature of about −20° C. or less.

8. The composite foam cushion of claim 1, wherein the crosslinker of the polymeric composition of the outer layer of the film is present in a greater weight percent than the crosslinker of the polymeric composition of the inner layer of the film.

9. The composite foam cushion of claim 1, wherein the film is bonded to the surface of the core of polymeric foam material.

10. The composite foam cushion of claim 1, wherein the crosslinker of the outer layer of the film is a carbodiimide based crosslinker.

11. The composite foam cushion of claim 10, wherein the crosslinker of the inner layer of the film is a carbodiimide based crosslinker.

12. The composite foam cushion of claim 1, wherein the crosslinker of the inner layer of the film is a carbodiimide based crosslinker.

13. A composite foam cushion for a sound control device, comprising:
a core formed of a polymeric foam material; and
a polymeric film overlaying a surface of the core of polymeric foam material;
wherein the composite foam cushion has a Conformability Gap Value of 0.650 inches or less.

14. The composite foam cushion of claim 13, wherein the polymeric film includes an inner layer facing the surface of the core of polymeric foam material and an outer layer positioned outward of the inner layer.

15. The composite foam cushion of claim 14, wherein:
the inner layer is formed of a polymeric composition including a crosslinker;
the outer layer is formed of a polymeric composition including a crosslinker; and
the inner layer of the film is less crosslinked than the outer layer of the film.

16. The composite foam cushion of claim 15, wherein the polymeric composition of the inner layer of the film and the polymeric composition of the outer layer of the film are both polyurethane based polymers.

17. The composite foam cushion of claim 15, wherein the crosslinker of the polymeric composition of the outer layer of the film is different than the crosslinker of the polymeric composition of the inner layer of the film.

18. A composite foam cushion for a sound control device, comprising:
a core formed of a polymeric foam material; and
a polymeric film overlying a surface of the core of polymeric foam material;
wherein the composite foam cushion has an average Indentation Force Ratio of 0.090 or less over a Protrusion Value range of 2.0 to 7.0 millimeters.

19. The composite foam cushion of claim 18, wherein the polymeric film includes an inner layer facing the surface of the core of polymeric foam material and an outer layer positioned outward of the inner layer.

20. The composite foam cushion of claim 19, wherein:
the inner layer is formed of a polymeric composition including a crosslinker;
the outer layer is formed of a polymeric composition including a crosslinker; and
the inner layer of the film is less crosslinked than the outer layer of the film.

* * * * *